United States Patent [19]
Waller et al.

[11] Patent Number: 5,922,785
[45] Date of Patent: Jul. 13, 1999

[54] DENTAL RESINS

[75] Inventors: Duncan E. Waller, Ypsilanti; Emil Jandourek, Livonia, both of Mich.

[73] Assignee: The Kerr Corporation, Orange, Calif.

[21] Appl. No.: 08/909,427

[22] Filed: Aug. 11, 1997

(Under 37 CFR 1.47)

[51] Int. Cl.$^6$ .............................. C09K 3/00; C08G 63/06
[52] U.S. Cl. ..................... 523/116; 523/117; 524/317; 524/599; 528/148; 433/228.1; 514/160
[58] Field of Search .................................. 523/116, 117; 524/317, 599; 433/228.1; 528/148; 514/160

[56] References Cited

U.S. PATENT DOCUMENTS

| | | |
|---|---|---|
| 2,516,438 | 7/1950 | Wheeler . |
| 3,047,408 | 7/1962 | Dougherty . |
| 4,240,832 | 12/1980 | Jandourek . |
| 4,375,968 | 3/1983 | Manhart . |
| 4,542,172 | 9/1985 | Jochum et al. . |
| 4,647,600 | 3/1987 | Kawahara et al. . |
| 4,652,593 | 3/1987 | Kawahara et al. . |
| 4,813,876 | 3/1989 | Wang . |
| 4,886,843 | 12/1989 | Walton . |
| 4,985,198 | 1/1991 | Hirasawa et al. . |
| 5,540,766 | 7/1996 | Castellani . |

*Primary Examiner*—Andrew E. C. Merriam
*Attorney, Agent, or Firm*—Wood, Herron & Evans, L.L.P.

[57] ABSTRACT

Dental resins and dental compositions utilizing such resins are described. The dental compositions are particularly useful as cavity liners and root canal sealants which contain calcium hydroxide (or calcium oxide) and which are utilized to deliver calcium to exposed dental pulp. The resins, and resin-containing compounds, include eutectic mixtures of polyfunctional salicylates. In particular, the transesterification of a blend of trimethylolpropane and neopentylglycol with methyl salicylate yields a blend of trimethylolpropanetrisalicylate and neopentylglycoldisalicylate, which is contemplated by the present invention.

18 Claims, No Drawings

DENTAL RESINS

FIELD OF THE INVENTION

The invention relates to resins useful in dental compositions, and more particularly to resins and dental compositions used to carry and deliver calcium compounds to the dentin.

BACKGROUND OF THE INVENTION

During various dental and endodontic treatments the pulp within the patient's teeth is exposed or nearly exposed. The tooth pulp is highly sensitive to heat and pressure because it contains the nerve endings of the tooth. Thus, it is desirable to protect this pulp during the filling of cavities, performance of root canals and other dental procedures. Several of the common practices for accomplishing this are described below.

It is known that calcium hydroxide may serve as a protective barrier for pulpal tissue against the attack of acids from certain filling materials used in the teeth by acting as a neutralizing agent. It is also known that calcium hydroxide has a stimulating effect which promotes the healing of dentin by promoting the formation of secondary dentin when the calcium hydroxide is applied near or on the exposed pulp.

For some time, dispersions of calcium hydroxide in aqueous or organic solutions of film-forming materials have been used for the treatment of tooth cavities as the vehicle for contacting the pulp with calcium hydroxide. Typically, however, when calcium hydroxide dispersions in aqueous or organic systems are used, the resultant cavity lining may not have sufficient mechanical strength to protect the tooth from the mechanical impact and stresses which occur during the filling operation.

One means for overcoming the deficiencies of some of the prior aqueous and organic solvent systems containing calcium hydroxide, was the combination of calcium hydroxide within self-hardening pastes. One such self-hardening system is described in U.S. Pat. No. 3,047,408. The '408 patent describes a dental composition that includes excess calcium hydroxide mixed with an ester of a polyhydric alcohol and salicylic acid or its esters. The mixture reacts to form a rigid and permeable mass of calcium phenolate having available calcium hydroxide dispersed therein. Another system of this general type is disclosed in U.S. Pat. No. 4,240,832. The system disclosed in the '832 patent comprises two pastes and is based upon calcium hydroxide and a condensate of an ester of salicylic acid and an aldehyde, such as formaldehyde or its oligomers.

Generally speaking, hardenable systems of the type disclosed in the '408 and '832 patents provide advantages vis-a-vis the earlier calcium hydroxide-containing systems and have found great use as dental cavity liners and pulp capping materials. In these dental cements, the "setting" of the cement is believed to occur through chelation binding of the calcium hydroxide or oxide with the salicylic acid esters to form an ionic lattice structure within the salicylate resin. Because the composition absorbs water, leaching of calcium and hydroxyl ions occurs, which has the beneficial and advantageous properties described hereinabove. However, such hardenable systems have certain disadvantages, including their susceptibility to attack by acids, discoloration, and water sorption.

What is needed are resins and dental compositions which include such resins that can be used to effectively deliver highly alkaline calcium compounds such as calcium hydroxide and/or calcium oxide.

SUMMARY OF THE INVENTION

The present invention is directed to resins particularly adapted for use in a variety of dental compositions, including cavity liners and root canal sealants. The resins of the present invention have specific utility in the context of dental compositions containing calcium hydroxide (or calcium oxide) and which are utilized to deliver the calcium compound to an exposed dental pulp.

The resins and dental compositions based thereon of the present invention possess many, if not all, of the advantages of prior known formaldehyde-derived resins, but do not require formaldehyde in their synthesis and thus do not present manufacturing and environmental problems. Additionally, the dental compositions of the present invention are easy-to-use two-paste compositions possessing rapid internal chelation, resistance to discoloration and acid-etching disintegration, a tendency to reduce tissue inflammation and promotion of secondary dentin formation.

It should be noted in the context of the present invention that calcium hydroxide is the calcium compound of choice. However, calcium oxide may be used as a slower reacting alternative since it converts to calcium hydroxide in the tooth structure by interaction with aqueous tubular fluid present in the dentin.

In a preferred embodiment, the resin of the present invention is formulated by the transesterification of a blend of trimethylolpropane and neopentylglycol with methyl salicylate, to yield a blend of trimethylolpropanetrisalicylate and neopentylglycoldisalicylate in a ratio ranging from 1:3 to 1:6. More preferably, the ratio of the two polysalicylates in the resin of the present invention is approximately 1:4.3, formulated using a molar ratio of 1:2.97 trimethylolpropane to neopentylglycol in the transesterification reaction. The novel blend of polysalicylates in the resin of the present invention has an optimized melting point depression level, which is approximately 40° F., and also contains the polysalicylate functionality necessary for intermolecular chelation bonding. Chelation utilizes a chelate, which is a type of coordination compound in which a polyvalent metal ion, such as calcium in this case, is attached by coordinate linkages to two or more non-metal atoms in an adjacent molecule or ligand, forming heterocyclic rings, with, in this invention, concurrent solidification. The chelate (calcium in this case) is thereby ionically bonded within the resin matrix and can leach out to provide the beneficial effects of solubilized calcium ions which are known in the art and described hereinabove. Titanium isopropoxide is one suitable catalyst useful in the synthesis of the resin blend of the present invention and catalyzes the transesterification of the trimethylolpropane and neopentylglycol with methyl salicylate. Upon completion of the transesterification reaction, any residual methyl salicylate in the resin mixture, which is liquid blend, is vacuumed stripped.

The resins of the present invention may be synthesized using other polyols besides those mentioned above to synthesize analogous polyfunctional salicylate resins. For example, it is contemplated that blends of salicylate esters of any diols or triols which eutectically liquefy at ambient temperatures are suitable in the context of the present invention. Furthermore, a suitable range of the ratio of the polysalicylates in the resin blend is from 1:1 to 1:10, depending upon the particular polysalicylates utilized.

Generally speaking, the resin blends of the present invention can be used in a variety of dental compositions in the amount of 15 to 50% by weight, wherein it is desirable to incorporate calcium hydroxide or calcium oxide in the amount of 45 to 55% by weight. In such dental compositions, the fillers used may be stoichiometric excesses of calcium hydroxide or calcium oxide, which are co-reactants in the composition, since they undergo a chelation reaction with the resin blend to initiate setting of the mixed paste. As is well known in the art, barium sulfate may be added as a radiopaqueing filler, titanium dioxide as a whitening filler, and zinc oxide as a consistency-modifying filler. Other known components are also contemplated, such as plasticizers.

These and other features and advantages of the present invention will become apparent to persons skilled in the art upon review of the following detailed description of the invention.

DETAILED DESCRIPTION OF THE INVENTION

In a preferred embodiment, the resins in accordance with this invention are synthesized by transesterification of neopentylglycol and trimethylolpropane with methyl salicylate, utilizing titanium isopropoxide as the catalyst. The resulting resin blend comprises trimethylolpropane trisalicylate and neopentylgylcol disalicylate. Since both of these polysalicylates when pure are low temperature melting crystalline solids (having melting points of 132° F. and 99° F., respectively), the blend of such resins liquefies at or below ambient temperatures due to mutual melting point depression. In fact, the melting point of the resins of the present invention is in the range of about 35° F. to 75° F. Also, due to their common polysalicylate functionality, these individual salicylates are capable of co-synthesis and purification. As will be described in greater detail below, the resin blend of the present invention has particular utility when mixed with a second paste component containing either calcium hydroxide or calcium oxide. Chelation hardening time increases with an increase in the size of the central alkyl moiety of the resin and compressive strength of the resultant chelated cement decreases.

EXAMPLE 1
Transesterification Synthesis of Resin Comprising Neopentylglycol Disalicylate and Trimethylolpropane Trisalicylate Blend The transesterification reaction mixture utilized to synthesize the resin blend of the present invention comprised the following:

| | |
|---|---|
| Methyl Salicylate | 82.0 parts by weight (1.5 stoichemetric excess) |
| Neopentylglycol | 13.5 parts by weight |
| Trimethylolpropane | 4.5 parts by weight; and |
| Titanium Isopropoxide | 0.05 parts by weight. |

The procedure utilized was as follows. All above-noted raw materials except the titanium isopropoxide were loaded into a Pfaudler reactor, a vacuum of approximately 9.3 mm Hg was applied, and the heat setting for the reactor was 212° F. After approximately 75 minutes, the reaction mixture reached 140° F. and the onset of distillation caused the splitter temperature to rise to 134° F. Once the distillate turned clear, which occurred after approximately one pound of distillate was generated, the vacuum was released and 100 grams of titanium isopropoxide was added to the reaction mixture. Up to this point, prior to adding the titanium isopropoxide, none of the polysalicylates have been formed. Thereafter, the reactor heater was set at 400° F. After three hours, the baffle temperature in the reactor reached 354° F. and the distillation of methanol, a byproduct of the transesterification reaction, caused the splitter temperature to rise to 158° F. The reaction was continued overnight and approximately 17 hours after commencement a drop of 20° in the splitter temperature indicated the completion of the transesterification reaction. The reason for this is that the transesterification reaction is exothermic, and upon its completion, the rate of distillation decreased markedly and the temperature in the splitter decreased. The reaction mixture was cooled to 187° F. and the vacuum was reapplied to strip off any unreacted methyl salicylate. During this stripping operation, the heater was reset to 325° F. and maintained at that temperature until the end of the vacuum distillation, which lasted approximately six hours. The following day, the resin was drained from the reactor at a baffle temperature of 150° F.

In a preferred embodiment, the trimethylol propane trisalicylate/neopentylgylcol disalicylate blend contains a ratio of the two polysalicylates of approximately 1:4.3. This ratio is achieved using a molar ratio of 1:2.97 trimethylolpropane to neopentylglycol for the transesterification reaction. It will be appreciated that the other polysalicylates can be used in the present invention. In fact, it is contemplated that blends of low melting point salicylate esters of virtually any other diols or triols which eutectically liquefy at ambient temperature can be used. Depending on the particular polysalicylate chosen, the molar ratio in the blend is in the range of 1:1 to 1:10.

In accordance with another aspect of the present invention, the resin blend as described hereinabove is useful in a variety of dental compositions, such as cavity liners and root canal sealants.

EXAMPLE 2
Cavity Liner Composition

In accordance with another aspect of the present invention, the novel polysalicylate resins of the invention can be used in cavity liners. The formulation for one preferred cavity liner composition is as follows:

| COMPONENT | WEIGHT PERCENT (%) |
|---|---|
| BASE PASTE | |
| Calcium hydroxide USP | 51.77 |
| Ethyltoluenesulfonamide | 33.93 |
| Zinc oxide USP | 14.05 |
| Zinc stearate | 0.25 |
| | 100.0 |
| CATALYST PASTE | |
| Polysalicylate resin blend | 45.00 |
| Barium sulfate | 37.80 |
| Titanium dioxide USP | 10.00 |
| Methyl salicylate NF | 5.00 |
| Sub-micron silica | 2.00 |
| Iron oxide pigment | 0.20 |
| | 100.00 |

The reference in the catalyst paste to the "polysalicylate resin blend" means the polysalicylate resin blends of the present invention.

EXAMPLE 3
Root Canal Sealant

The present invention further contemplates use of the polysalicylate resin blends of the invention in root canal sealant formulations. One such formulation is as follows:

| COMPONENT | WEIGHT PERCENT (%) |
|---|---|
| BASE PASTE | |
| Calcium oxide | 48.50 |
| Ethyltoluene sulfonamide | 34.98 |
| Zinc oxide USP | 12.99 |
| Zinc stearate | 2.00 |
| Sub-micron silica | 1.53 |
| | 100.00 |
| CATALYST PASTE | |
| Polysalicyalte resin blend | 45.00 |
| Barium sulfate | 39.80 |
| Sub-micron silica | 6.00 |
| Isobutyl salicylate | 5.00 |
| Titanium dioxide USP | 4.00 |
| Iron oxide pigment | 0.20 |
| | 100.00 |

EXAMPLE 4

Root Canal Sealant

An alternative root canal sealant formulation of the present invention is as follows:

| COMPONENT | WEIGHT PERCENT (%) |
|---|---|
| BASE PASTE | |
| Calcium oxide | 48.96 |
| Ethyltoluene sulfonamide | 48.83 |
| Dimer acid resin | 1.23 |
| Zinc stearate | 0.98 |
| | 100.00 |
| CATALYST PASTE | |
| Bismuth trioxide | 43.05 |
| Polysalicylate resin blend | 19.65 |
| Barium sulfate | 18.71 |
| Isobutyl salicylate | 13.10 |
| Sub-micron silica | 5.49 |
| | 100.00 |

The dimer acid resin component of the base paste is a purified natural resin, such as naturally occurring tree resin, containing predominantly high molecular weight dimer acids. Such resins have been used as friability reducers in dental materials for years, and are particularly useful in reducing brittleness of mixed and chelated solid materials. One particular dimer acid resin suitable for use in the present invention is polypale resin available from Hercules.

While the invention has been described with reference to specific compositions and formulations, persons skilled in the art will recognize that variations and modifications to the specific examples disclosed are contemplated. Thus, the invention is not to be limited to the specifics, but rather is to be construed in accordance with the appended claims.

What is claimed is:

1. A dental resin, comprising:
    a eutectic blend of poly-functional salicylates.
2. A dental resin according to claim 1 wherein said blend of polyfunctional salicylates includes trimethylolpropane trisalicylate.
3. A dental resin according to claim 1 wherein said blend of polyfunctional salicylates includes neopentylglycol disalicylate.
4. A dental resin according to claim 1 wherein said blend of polyfunctional salicylates includes trimethylolpropane trisalicylate and neopentylglycol disalicylate.
5. A dental resin according to claim 4 wherein the ratio of resins in said blend is in the range of about 1:3 to 1:6 trimethylolpropane trisalicylate to neopentylglycol disalicylate.
6. A dental resin according to claim 4 wherein the ratio of resins in said blend is in the range of about 1:4.3 trimethylolpropane trisalicylate to neopentylglycol disalicylate.
7. A dental resin according to claim 1 wherein said blend of polyfunctional salicylates includes at least two salicylate esters of diols or triols, which blend eutectically liquefies at ambient temperatures.
8. A dental composition, comprising:
    a resin blend of at least two polyfunctional salicylates;
    a calcium-containing compound;
    at least one filler; and
    a water miscible plasticizer.
9. A dental composition according to claim 8 wherein said calcium-containing compound is selected from the group consisting of calcium hydroxide and calcium oxide.
10. A dental composition according to claim 8 wherein said resin blend includes trimethylolpropane trisalicylate.
11. A dental composition according to claim 8 wherein said resin blend includes neopentylglycol disalicylate.
12. A dental composition according to claim 8 wherein said resin blend includes trimethylolpropane trisalicylate and neopentylglycol disalicylate.
13. A dental composition according to claim 12 wherein said resin blend components are present in a ratio in the range of about 1:3 to 1:6 trisalicylate to disalicylate.
14. A dental composition according to claim 12 wherein said resin blend components are present in a ratio in the range of about 1:4.3 trisalicylate to disalicylate.
15. A dental composition according to claim 8 wherein said resin blend includes at least two salicylate esters of diols or triols, which blend eutectically liquefies at ambient temperatures.
16. A dental composition according to claim 8 wherein said at least one filler includes a whitening filler and a radiopacifying filler.
17. A dental composition according to claim 8 wherein said resin blend is present in the range of about 15–50% by weight.
18. A dental composition according to claim 8 wherein said calcium-containing compound is present in the range of about 45–55% by weight.

* * * * *